(12) United States Patent
Lambert et al.

(10) Patent No.: US 7,566,809 B2
(45) Date of Patent: *Jul. 28, 2009

(54) PROCESS FOR SEPARATION OF A MIXTURE COMPRISING AT LEAST ONE HYDROFLUOROALKANE

(75) Inventors: Alain Lambert, Beauvechain (BE); Vincent Wilmet, Wavre (BE)

(73) Assignee: Solvay S.A. (BE)

( * ) Notice: Subject to any disclaimer, the term of this patent is extended or adjusted under 35 U.S.C. 154(b) by 0 days.

This patent is subject to a terminal disclaimer.

(21) Appl. No.: 11/753,970

(22) Filed: May 25, 2007

(65) Prior Publication Data

US 2008/0033219 A1    Feb. 7, 2008

Related U.S. Application Data

(60) Division of application No. 11/476,306, filed on Jun. 28, 2006, now Pat. No. 7,223,892, which is a continuation of application No. 10/282,785, filed on Oct. 29, 2002, now Pat. No. 7,074,434, which is a division of application No. 09/868,368, filed as application No. PCT/EP99/10173 on Dec. 16, 1999, now Pat. No. 6,521,803.

(30) Foreign Application Priority Data

Dec. 18, 1998  (BE) ................... 9800910

(51) Int. Cl.
    C07C 17/20    (2006.01)
(52) U.S. Cl. .............. 570/164; 570/165; 570/163; 570/170; 570/175
(58) Field of Classification Search .......... 570/164, 570/165, 163, 170, 175
    See application file for complete search history.

(56) References Cited

U.S. PATENT DOCUMENTS

| | | | |
|---|---|---|---|
| 3,381,044 | A | 4/1968 | Wiedemann et al. |
| 5,276,225 | A | 1/1994 | Berthe |
| 5,414,165 | A | 5/1995 | Nappa et al. |
| 5,461,177 | A | 10/1995 | Manzer et al. |
| 5,739,406 | A | 4/1998 | Pennetreau et al. |
| 6,540,882 | B1 | 4/2003 | Reif et al. |
| 6,730,817 | B1 | 5/2004 | Wilmet et al. |
| 7,223,892 | B2 * | 5/2007 | Lambert et al. |

FOREIGN PATENT DOCUMENTS

| | | |
|---|---|---|
| EP | 0 699 649 | 3/1996 |
| EP | 0 601 373 | 2/1997 |
| JP | 10101593 | 4/1998 |
| WO | WO-91/04955 | 4/1991 |
| WO | WO-97/05089 | 2/1997 |
| WO | WO-97/13719 | 4/1997 |
| WO | WO-97/15540 | 5/1997 |
| WO | WO-98/21171 | 5/1998 |
| ZA | 9608481 | 5/1997 |

OTHER PUBLICATIONS

Okamoto Shuichi, Pat. Abs. of Japan vol. 1998: No. 9, Abs. of JP 10-101593, Production of 1,1,1,3,3-Pentafluoropropane,: (Apr. 21, 1998).

* cited by examiner

*Primary Examiner*—Elvis O Price
(74) *Attorney, Agent, or Firm*—Connelly Bove Lodge & Hutz LLP

(57) ABSTRACT

Process for the separation of a mixture comprising at least one hydrofluoroalkane and hydrogen fluoride, according to which a hydrofluoroalkane/hydrogen fluoride mixture is reacted with at least one chlorinated or chlorofluorinated precursor of the hydrofluoroalkane. Process for the preparation of a hydrofluoroalkane comprising such a separation, in combination with a catalytic reaction stage. Azeotropic compositions.

20 Claims, 4 Drawing Sheets

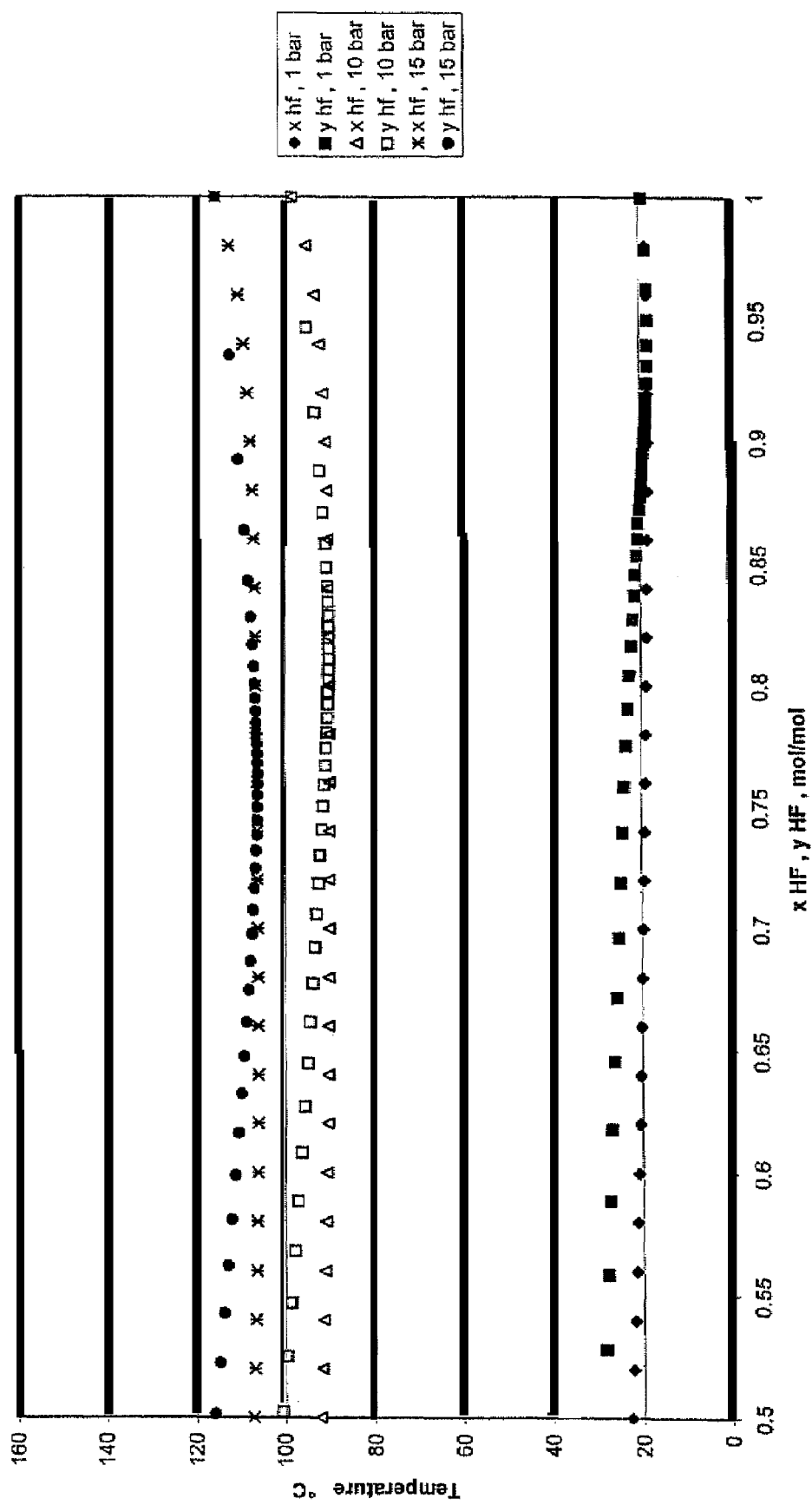

PROCESS FOR SEPARATION OF A MIXTURE COMPRISING AT LEAST ONE HYDROFLUOROALKANE

RELATED APPLICATIONS

Figure 1:
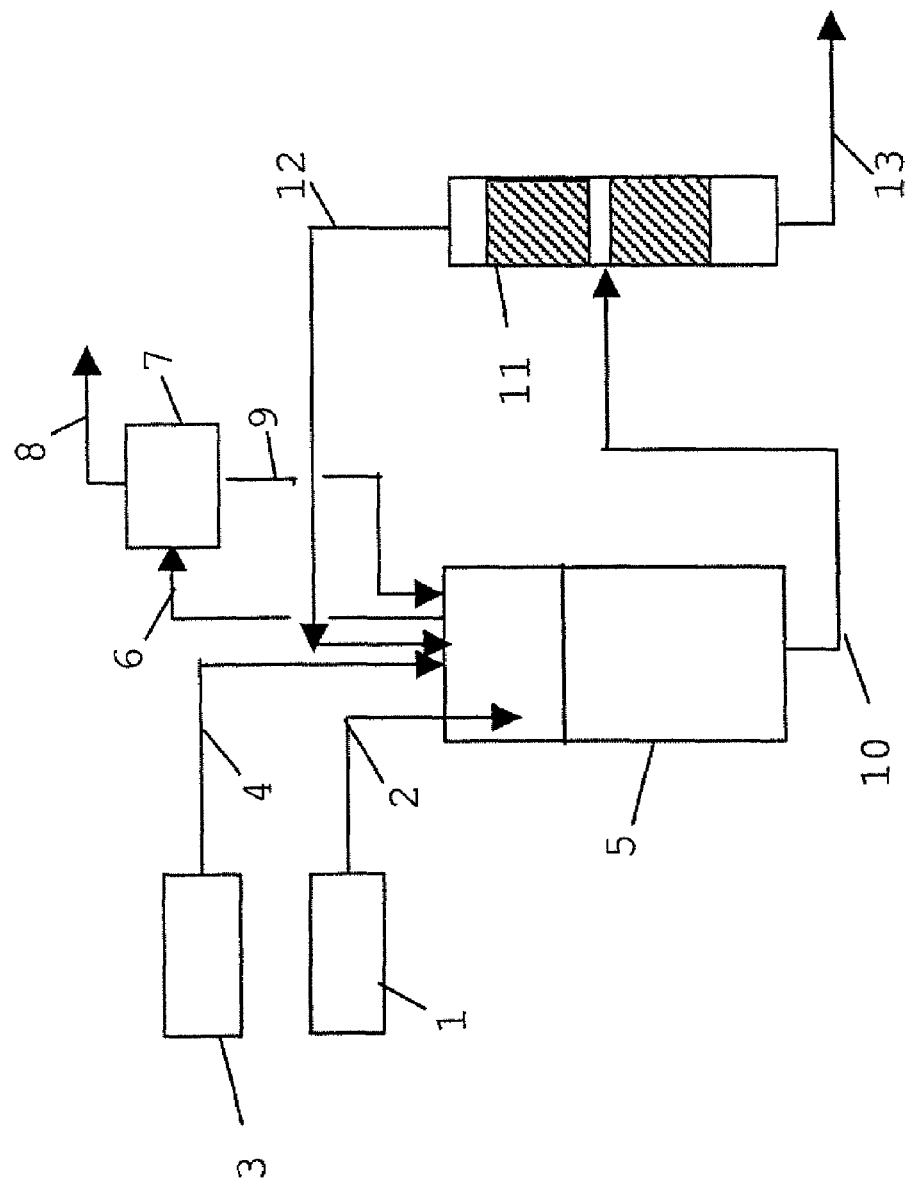

This application is a divisional of U.S. patent application Ser. No. 11/476,306, filed Jun. 28, 2006, now U.S. Pat. No. 7,223,892 which is a continuation of U.S. Pat. application Ser. No. 10/282,785, filed Oct. 29, 2002, now U.S. Pat. No. 7,074,434, which is a divisional of U.S. patent application Ser. No. 09/868,368, filed Jul. 17, 2001, now U.S. Pat. No. 6,521,803 which is a §371 of PCT/EP99/10173, filed Dec. 16, 1999 which claims benefit to Belgium application 09800910 filed Dec. 18, 1998.

The present invention relates to a process for the separation of a mixture comprising a hydrofluoroalkane and hydrogen fluoride, as well as to processes for the preparation of a hydrofluoroalkane and to azeotropic compositions.

BACKGROUND OF THE INVENTION

Hydrofluoroalkanes can be prepared by reaction of an appropriate chlorinated precursor with hydrogen fluoride, as disclosed, for example, in Patent Applications EP-A1-0,699,649 and WO-A1-97/15540 (on behalf of Solvay) and in Patent Application WO-A1-97/05089. In such a process, at the outlet of the reactor, the mixture of reaction products comprises, in addition to the desired hydrofluoroalkane, hydrogen chloride originating from the removal of the chlorine atom or atoms from the starting chlorinated precursor, hydrogen fluoride, chlorofluorinated intermediates, generally unconverted chlorinated precursor, possibly inert diluents, and various byproducts in small amounts. Given that the operation is usually carried out with an excess of hydrogen fluoride with respect to the chlorinated precursor, unconverted hydrogen fluoride is generally present in the mixture of reaction products. Whereas the majority of the constituents of the mixture of reaction products can be easily and completely separated by distillation, complete separation between the hydrofluoroalkane and the hydrogen fluoride is generally very difficult to achieve by distillation, this being because these compounds often form azeotropic mixtures. Patent Application WO-A1-97/05089 discloses a process for the purification of hydro-(chloro)fluoroalkanes (in particular 1,1,1,3,3-pentafluoropropane or HFC-245fa) from azeotropic mixtures with hydrogen fluoride by an azeotropic distillation technique comprising two successive stages of distillation at different temperatures and at different pressures.

However, this azeotropic distillation technique exhibits the disadvantages of requiring a large difference in temperature or in pressure between the two columns, so as to have available a sufficient separation potential (difference in composition between the low pressure/temperature azeotrope and the high pressure/temperature azeotrope), and of producing a high recycling flow rate between the two columns.

Patent Application WO-A1-97/13719 discloses a process for the separation and recovery of hydrogen fluoride from its (azeotropic) mixtures with, inter alia, hydrofluoroalkanes comprising from 1 to 6 carbon atoms (in particular HFC-245fa). The mixture is brought into contact with an alkali metal fluoride (in particular, potassium fluoride or caesium fluoride) solution and the organic phase is separated from the phase comprising the hydrogen fluoride and the alkali metal fluoride.

Through this known process, contamination of the organic phase by the potassium fluoride or caesium fluoride and the risk of decomposition of the hydrofluoroalkanes which this contamination might bring about may be feared. Moreover, these alkali metal fluorides, and more particularly caesium fluoride, are very expensive.

SUMMARY OF THE INVENTION

An object of the present invention is to provide a process for the separation of a mixture comprising at least one hydrofluoroalkane, preferably comprising from 3 to 6 carbon atoms, and hydrogen fluoride which does not exhibit the disadvantages of the abovementioned processes.

The invention consequently relates to a process for the separation of a mixture comprising at least one hydrofluoroalkane and hydrogen fluoride, hereinafter known as hydrofluoroalkane/hydrogen fluoride mixture, according to which the hydrofluoroalkane/hydrogen fluoride mixture is reacted with at least one organic compound capable of reacting with hydrogen fluoride.

A BRIEF DESCRIPTION OF THE FIGURES

FIGS. 1 to 4 respectively illustrate specific embodiments of the process for the separation of a mixture comprising at least one hydrofluoroalkane and hydrogen fluoride, of the process for the manufacture of a hydrofluoroalkane and the azeotropic or pseudoazeotropic compositions in accordance with the present invention.

A DETAILED DESCRIPTION OF THE INVENTION

The reaction of the hydrofluoroalkane/hydrogen fluoride mixture with at least one organic compound capable of reacting with hydrogen fluoride makes it possible to consume at least a portion of the hydrogen fluoride. The separation process according to the invention thus provides a mixture of reaction products which is depleted in hydrogen fluoride. This is of advantage in the context of a hydrofluoroalkane synthesis, it being possible for the said mixture to be used in particular as extraction solvent. The mixture of reaction products obtained is also highly suitable as starting material when it is subjected to at least one subsequent stage of treatment intended to recover the hydrofluoroalkane. Hydrofluoroalkane essentially devoid of hydrogen fluoride can thus be obtained.

A specific advantage arises when the hydrofluoroalkane is capable of forming an azeotrope or pseudoazeotrope with hydrogen fluoride because it is possible to "break" such an azeotrope, that is to say that the separation process according to the invention is capable of providing a mixture in which the hydrofluoroalkane and the hydrogen fluoride are present in proportions different from those for which they form an azeotrope or a pseudoazeotrope.

The term "hydrofluoroalkane" is understood to denote the hydrocarbonaceous compounds corresponding to the general formula $C_aH_{(2a+2)-b}F_b$ in which a=1 to 6 and b=1 to 2a+1. The hydrofluoroalkanes which comprise from 3 to 6 carbon atoms are preferred. The hydrofluoroalkanes which comprise from 3 to 4 carbon atoms are particularly preferred.

Mention may be made, as examples of hydrofluoroalkanes which can be separated from mixtures with hydrogen fluoride by the separation process according to the invention, of 1,1,1,3,3-pentafluoropropane (HFC-245fa), 1,1,2,2,3-pentafluoropropane (HFC-245ca), 1,1,1,2,3-pentafluoropropane (HFC-245eb), 1,1,1,3,3,3-hexafluoropropane (HFC-236fa), 1,1,1,2,3,3-hexafluoropropane (HFC-236ea), 1,1,1,2,3,3,3- heptafluoropropane (HFC-227ea), 1,1,1,3,3-pentafluoro-2-methylpropane (HFC-365mps), 1,1,1,3,3-pentafluorobutane (HFC-365mfc), 1,1,1,4,4,4-hexafluorobutane (HFC-356mff) and 1,1,1,2,3,4,4,5,5,5-decafluoropentane (HFC-43-10mee). Among these compounds, 1,1,1,3,3-pentafluoropropane (HFC-245fa) and 1,1,1,3,3-pentafluorobutane (HFC-365mfc) are particularly preferred. 1,1,1,3,3-Pentafluorobutane (HFC-365mfc) is very particularly preferred.

The organic compounds used in the separation process according to the invention are capable of reacting with hydrogen fluoride. Organic compound examples are, inter alia, linear or branched alkanes comprising from 1 to 10 carbon atoms which are preferably chlorinated and/or brominated and optionally substituted, and optionally substituted alkenes comprising from 2 to 10 carbon atoms. A chlorinated or chlorofluorinated organic compound is often employed. Halogenated olefins, such as chlorinated, fluorinated or chlorofluorinated olefins, such as, for example, vinyl chloride, vinylidene chloride, trichloroethylene, perchloroethylene, vinylidene fluoride and chlorotrifluoroethylene or fluoropropenes, such as, for example, hexafluoropropene, are well suited, for example.

The organic compound is preferably a chlorinated or chlorofluorinated precursor of the hydrofluoroalkane.

The term "chlorinated or chlorofluorinated precursor of the hydrofluoroalkane" is understood to denote hydrochloroalkanes and hydrochlorofluoroalkanes, that is to say, respectively, chlorinated and chlorofluorinated hydrocarbonaceous compounds comprising at least one chlorine atom and at least one hydrogen atom, the same number of carbon atoms as the desired hydrofluoroalkane and at least one fluorine atom less than the desired hydrofluoroalkane. The desired hydrofluoroalkane can be obtained, starting from at least one chlorinated or chlorofluorinated precursor of the hydrofluoroalkane, by a reaction of this precursor with hydrogen fluoride.

Mention may be made, as examples of chlorinated or chlorofluorinated precursors of hydrofluoroalkanes which can be used in the separation process according to the invention, of hydrochloroalkanes, such as 1,1,1,3,3-pentachloropropane (HCC-240fa), 1,1,2,2,3-pentachloropropane (HCC-240aa), 1,1,1,2,3-pentachloropropane (HCC-240db), 1,1,1,3,3,3-hexachloropropane (HCC-230fa), 1,1,1,2,3,3-hexachloropropane (HCC-230da), 1,1,1,2,3,3,3-heptachloropropane (HCC-220da), 1,1,1,3,3-pentachloro-2-methylpropane (HCC-360jns), 1,1,1,3,3-pentachlorobutane (HCC-360jfa), 1,1,1,4,4,4-hexachlorobutane (HCC-350jff) and 1,1,1,2,3,4,4,5,5,5-decachloropentane (HCC-430jdd), and of hydrochlorofluoroalkanes, such as 1-fluoro-1,1,3,3-tetrachlorobutane (HCFC-361kfa), 3-fluoro-1,1,1,3-tetrachlorobutane (HCFC-361jfb), 1,1-difluoro-1,3,3-trichlorobutane (HCFC-3621fa), 1,3-difluoro-1,1,3-trichlorobutane (HCFC-362kfb), 3,3-difluoro-1,1,1-trichlorobutane (HCFC-362jfc), 1,1-dichloro-1,3,3-trifluorobutane (HCFC-363kfc), 1,3-dichloro-1,1,3-trifluorobutane (HCFC-363lfb), 3,3-dichloro-1,1,1-trifluorobutane (HCFC-363mfa), 1-chloro-1,1,3,3-tetrafluorobutane (HCFC-364lfc) and 3-chloro-1,1,1,3-tetrafluorobutane (HCFC-364mfb).

In an alternative form, the term "chlorinated or chlorofluorinated precursor of the hydrofluoroalkane" is understood to denote (hydro)chloroalkenes and (hydro)chlorofluoroalkenes, that is to say, respectively, chlorinated and chlorofluorinated carbonaceous compounds comprising at least one chlorine atom and optionally at least one hydrogen atom, the same number of carbon atoms as the desired hydrofluoroalkane and at least one fluorine atom less than the desired hydrofluoroalkane. Mention may be made, for example, of (hydro)chloro(fluoropropenes, such as, for example, 1-chloro-3,3,3-trifluoroprop-1-ene as precursor of 1,1,1,3,3-pentafluoropropane, and of (hydro)chloro(fluoro)butenes, such as, for example, dichlorodifluorobutenes, such as, in particular, 1,1-dichloro-1,3-difluorobut-2-ene, and/or chlorotrifluorobutenes, such as, in particular, 1-chloro-1,1,3trifluorobut-2-ene, as precursors of 1,1,1,3,3-pentafluorobutane.

In the separation process according to the invention, the reaction between the hydrofluoroalkane/hydrogen fluoride mixture and the organic compound is preferably carried out in the liquid phase.

In the separation process according to the invention, the reaction between the hydrofluoroalkane/hydrogen fluoride mixture and the organic compound can be carried out in the presence of a catalyst. It can also be carried out in the absence of catalyst.

When the reaction between the hydrofluoroalkane/hydrogen fluoride mixture and the organic compound is carried out in the presence of a catalyst, use may be made of catalysts which can promote the substitution of a chlorine atom by a fluorine atom. Mention may be made, among the catalysts which can be used, of derivatives of metals chosen from the metals from groups IIIa, IVa and b, Va and b, and VIb of the Periodic Table of the Elements and their mixtures. Titanium, tantalum, molybdenum, boron, tin and antimony derivatives are more especially selected. Use is preferably made of titanium or tin derivatives. Titanium derivatives are particularly well suited. Mention may be made, as derivatives of the metals, of salts and more particularly of halides. The choice is preferably made among chlorides, fluorides and chlorofluorides. Titanium and tin chlorides, fluorides and chlorofluorides and their mixtures are particularly preferred catalysts in the process for the preparation of a hydrofluoroalkane according to the invention. Titanium tetrachloride and tin tetrachloride are particularly well suited.

When the reaction between the hydrofluoroalkane/hydrogen fluoride mixture and the organic compound is carried out in the liquid phase, it is preferably carried out in the absence of catalyst, which makes it possible to draw off the reaction mixture in the liquid phase and, if appropriate, to carry out one or more easy subsequent distillation stages.

The molar ratio of the hydrogen fluoride to the hydrofluoroalkane in the hydrofluoroalkane/hydrogen fluoride mixture to be separated by the separation process according to the invention is variable. The hydrogen fluoride can be in excess with respect to the hydrofluoroalkane in the hydrofluoroalkane/hydrogen fluoride mixture to be separated by the separation process according to the invention. The separation process according to the invention is highly suitable when the hydrofluoroalkane is capable of forming an azeotrope or a pseudoazeotrope with the hydrogen fluoride. The separation process according to the invention is preferably applied to a hydrofluoroalkane/hydrogen fluoride mixture with the azeotropic composition or a composition close to the azeotropic composition.

The separation process according to the invention finds an advantageous use in the separation of the mixture comprising 1,1,1,3,3-pentafluorobutane (HFC-365mfc) and hydrogen fluoride.

At a pressure of 3 bar, the composition of the hydrogen fluoride/1,1,1,3,3-pentafluorobutane azeotropic mixture is approximately 60/40% by weight, i.e. a hydrogen fluoride/1,1,1,3,3-pentafluorobutane molar ratio of approximately 11 mol/mole.

In a preferred embodiment of the invention, the mixture comprising 1,1,1,3,3-pentafluorobutane and hydrogen fluoride is separated by the reaction of the 1,1,1,3,3-pentafluorobutane/hydrogen fluoride mixture with a precursor of the 1,1,1,3,3-pentafluorobutane, preferably 1,1,1,3,3-pentachlorobutane, in the absence of catalyst. 1,1,1,3,3-Pentachlorobutane can be obtained, for example, by telomerization of chlorinated compounds, such as, for example, 2-chloropropene with carbon tetrachloride or vinylidene chloride with 1,1,1-trichloroethane, in the presence of various catalysts, such as, in particular, iron pentacarbonyl or copper salts in combination with an amine.

In the separation process according to the invention, the hydrofluoroalkane/hydrogen fluoride mixture and the organic compound are employed in proportions such that the molar ratio of the hydrogen fluoride to the organic compound is generally at least 0.5 mol/mole. The operation is preferably carried out with a molar ratio of the hydrogen fluoride to the organic compound of at least 1 mol/mole. In a more particularly preferred way, the operation is carried out with a molar ratio of the hydrogen fluoride to the organic compound of at least 3 mol/mole. In a very particularly preferred way, the operation is carried out with a molar ratio of the hydrogen fluoride to the organic compound of at least 5 mol/mole. The molar ratio of the hydrogen fluoride to the organic compound employed generally does not exceed 15 mol/mole. It is preferable for this molar ratio not to exceed 10 mol/mole.

The temperature at which the reaction between the hydrofluoroalkane/hydrogen fluoride mixture and the organic compound is carried out is generally at least 60° C. The temperature is preferably at least 80° C. In general, the temperature does not exceed 160° C. It preferably does not exceed 140° C.

The reaction between the hydrofluoroalkane/hydrogen fluoride mixture and the organic compound in the separation process according to the invention is preferably carried out in the liquid phase. In this case, the pressure is chosen so as to keep the reaction mixture in the liquid form. The pressure employed varies according to the temperature of the reaction mixture. It is generally less than or equal to 40 bar. It is preferably less than or equal to 35 bar. In a particularly advantageous way, the pressure is less than or equal to 25 bar. The pressure is generally greater than or equal to 5 bar. The pressure is preferably greater than or equal to 10 bar.

The separation process according to the invention can be carried out batchwise or continuously.

When the separation process according to the invention is carried out batchwise, the duration of the reaction between the hydrofluoroalkane/hydrogen fluoride mixture and the organic compound generally varies from 10 min to 5 h. This duration is preferably at least 0.5 h. This duration is advantageously at least 1 h. This duration generally does not exceed 4 h. This duration preferably does not exceed 2.5 h.

When the separation process according to the invention is carried out continuously, the residence time of the reactants in the reactor is generally at least 0.5 h. It usually does not exceed 30 h. It typically varies from 5 to 25 h. It preferably varies from 10 to 20 h. The term "residence time of the reactants in the reactor" is understood to denote the ratio of the volume of the reaction mixture to the flow rate by volume of the reaction mixture at the outlet of the reactor.

In the case where the hydrofluoroalkane is 1,1,1,3,3-pentafluorobutane and the organic compound is 1,1,1,3,3-pentachlorobutane, good results are obtained with a molar ratio of the hydrogen fluoride to the 1,1,1,3,3-pentachlorobutane of less than 15 mol/mole, preferably varying from 5 to 10 mol/mole, with a reaction temperature varying from 80 to 140° C., preferably from 110 to 120° C., at a pressure of 5 to 40 bar, preferably of 15 to 25 bar, and with a residence time of the reactants in the reactor of 0.5 to 25 h.

The reaction between the hydrofluoroalkane/hydrogen fluoride mixture and the organic compound in the process according to the invention can be carried out in any reactor constructed from a material resistant to the temperature, to the pressure and to the reactants which are used, in particular to hydrogen fluoride.

Advantageously, all or part of the hydrogen chloride formed by the reaction is continuously removed. Generally, at least 80% of the hydrogen chloride is removed.

In an alternative form of the process according to the invention which is preferred, the mixture of reaction products obtained in the reaction of the hydrofluoroalkane/hydrogen fluoride mixture with at least one organic compound capable of reacting with hydrogen fluoride is subjected to at least one subsequent treatment stage intended to recover the hydrofluoroalkane. Examples of treatment stages which can be used are, inter alia, treatments which can be used to separate hydrofluoroalkane from the residual hydrogen fluoride, such as, for example, adsorption on a solid, such as NaF, washing with water, an extraction operation, separation by an appropriate membrane, extractive distillation or at least one distillation. Among these treatments, distillation has given good results.

In an alternative form, a three-stage distillation is employed. A first distillation stage (I) is intended to recover at least one fraction comprising the residual hydrogen fluoride. A second distillation stage (II) is intended to recover at least one fraction comprising the non-volatile impurities. A third distillation stage (III) is intended to recover at least one fraction composed of the essentially pure hydrofluoroalkane. Any sequence of these distillations can be adopted which gives a satisfactory separation result and which makes possible the recovery of at least one fraction comprising essentially pure hydrofluoroalkane. A sequence in which first the stage (I), subsequently the stage (III) and subsequently the stage (II) are carried out has given good results.

In a specific embodiment, the invention consequently relates to a process for the separation of a mixture comprising at least one hydrofluoroalkane and hydrogen fluoride, according to which the said mixture is reacted with at least one chlorinated or chlorofluorinated precursor of the hydrofluoroalkane and, subsequently, the hydrofluoroalkane, depleted in hydrogen fluoride, is recovered, preferably by subjecting the mixture of the reaction products obtained to at least one distillation.

In the alternative form of the separation process according to the invention which is carried out in the absence of catalyst, the reaction mixture is advantageously drawn off from the reactor in the liquid form and then subjected to at least one distillation stage.

Another object of the present invention is to provide a process for the preparation of a hydrofluoroalkane starting from a chlorinated or chlorofluorinated precursor of the hydrofluoroalkane and from hydrogen fluoride.

The invention consequently relates to a process for the preparation of a hydrofluoroalkane, according to which, in a first reaction stage, at least one chlorinated or chlorofluorinated precursor of the hydrofluoroalkane is reacted with hydrogen fluoride and, in a subsequent reaction stage, at least a portion of the products formed during the first stage is reacted with hydrogen fluoride, one of the reaction stages optionally comprising a separation process according to the invention.

Generally, in the preparation process according to the invention, hydrofluoroalkane is formed in the first reaction stage and in the subsequent reaction stage. A conversion to hydrofluoroalkane of the sum of the chlorinated or chlorofluorinated precursors employed in each stage of at least 5 mol % is often maintained. The conversion is more often maintained at at least 10 mol %. The conversion is preferably maintained at at least 20 mol %. In a particularly preferred way, the conversion is maintained at at least 50 mol %.

The conversion to hydrofluoroalkane of the sum of the chlorinated or chlorofluorinated precursors employed in each stage is preferably different in the first reaction stage and in the subsequent reaction stage. In this case, a conversion as described above is often maintained in the first stage and a second, higher, conversion is maintained in the subsequent stage. This second conversion of the sum of the chlorinated or chlorofluorinated precursors employed in this second stage is often at least 70 mol %. The second conversion is preferably at least 90 mol %.

The content of hydrogen fluoride in the reaction mixture is generally different in the first reaction stage than in the subsequent stage. This content is preferably low in the first reaction stage and high in the subsequent stage.

The content of hydrogen fluoride in the reaction mixture of the first reaction stage is generally at least 5% by weight. The content is preferably at least 10% by weight. The content is generally at most 20% by weight. It is preferably at most 15% by weight.

The content of hydrogen fluoride in the reaction mixture of the subsequent reaction stage is generally at least 40% by weight. The content is preferably at least 60% by weight. The content is generally at most 75% by weight. It is preferably at most 70% by weight.

The preparation process can comprise catalytic reaction stages and/or reaction stages carried out in the absence of catalyst In an alternative form which is preferred, the preparation process according to the invention comprises at least one reaction stage carried out in the absence of catalyst and at least one catalytic reaction stage.

For simplicity, the continuation of the description relates solely to this preferred form of the preparation process according to the invention, without, however, limiting the scope thereof to this preferred form.

As regards the reaction stage carried out in the absence of catalyst, the preferred reaction conditions correspond to the conditions described above for the reaction between the hydrofluoroalkane/hydrogen fluoride mixture and the organic compound in the separation process according to the invention.

The two reaction stages are preferably carried out in the liquid phase and the hydrofluoroalkane/hydrogen fluoride mixture is drawn off from the catalytic reaction stage in the gaseous form, generally in the form of an azeotropic composition.

The hydrofluoroalkanes which can be prepared by the preparation process according to the invention are the same as the hydrofluoroalkanes which can be separated from their mixtures with hydrogen fluoride by the separation process according to the invention and which are mentioned above.

The chlorinated or chlorofluorinated precursors which can be used in the catalytic and non-catalytic reaction stages of the process for the preparation of a hydrofluoroalkane according to the invention are the same as the chlorinated or chlorofluorinated precursors which can be used in the separation process according to the invention and which are mentioned above. The chlorinated or chlorofluorinated precursor used in the catalytic reaction stage preferably comprises a mixture of chlorofluorinated intermediates formed in the non-catalytic reaction stage by the reaction of at least a portion of the hydrogen fluoride of a hydrofluoroalkane/hydrogen fluoride mixture with a chlorinated or chlorofluorinated precursor of the hydrofluoroalkane; the non-catalytic reaction stage of the preparation process then corresponds to the reaction of the separation process according to the invention described above.

The various treatment stages which can be used in the separation process according to the invention also apply, if appropriate, to the present process for the preparation of a hydrofluoroalkane.

The preparation process according to the invention is particularly efficient in the preparation of 1,1,1,3,3-pentafluorobutane.

When the preparation process according to the invention is applied to the preparation of 1,1,1,3,3-pentafluorobutane, the precursor of the hydrofluoroalkane used in the catalytic reaction stage can be 1,1,1,3,3-pentachlorobutane, a mixture of chlorofluorinated intermediates or a mixture of these products with 1,1,1,3,3-pentachlorobutane. The chlorofluorinated intermediates formed in the non-catalytic reaction stage of the process are essentially isomers of HCFC-363 and HCFC-364, that is to say 1,1-dichloro-1,3,3-trifluorobutane (HCFC-363kfc), 1,3-dichloro-1,1,3-trifluorobutane (HCFC-363lfb), 3,3-dichloro-1,1,1-trifluorobutane (HCFC-363mfa), 1-chloro-1,1,3,3-tetrafluorobutane (HCFC-364 lfc) or 3-chloro-1,1,1,3-tetrafluorobutane (HCFC-364 mfb) or a mixture of these compounds.

Other intermediates optionally present are (hydro)chloro(fluoro)butenes, such as, for example, 1,1-dichloro-1,3-difluorobut-2-ene and/or 1-chloro-1,1,3-trifluorobut-2-ene.

When the preparation process according to the invention is applied to the preparation of 1,1,1,3,3-pentafluorobutane, the precursor of the hydrofluoroalkane used in the non-catalytic reaction stage of the process is preferably 1,1,1,3,3-pentachlorobutane.

Use may be made, as catalyst of the reaction of the catalytic reaction stage of the process for the preparation of a hydrofluoroalkane according to the invention, of, for example, the catalysts mentioned above as catalysts which can be used in the separation process according to the invention.

The amount of catalyst employed in the catalytic reaction stage of the process for the preparation of a hydrofluoroalkane according to the invention can vary within wide limits. It is generally at least 0.5 mol %. It is preferably at least 2 mol %. In a more than preferred way, it is at least 5 mol %. It generally does not exceed 30 mol %. It preferably does not exceed 20 mol %. In a more than preferred way, it does not exceed 10 mol %. In the catalytic reaction stage, hydrogen fluoride is employed in an amount such that the molar ratio of the hydrogen fluoride to the chlorinated or chlorofluorinated precursor of the hydrofluoroalkane is generally at least 3 mol/mole. The operation is preferably carried out with a molar ratio of at least 5 mol/mole. This molar ratio generally does not exceed 15 mol/mole. It preferably does not exceed 10 mol/mole.

The temperature at which the reaction of the catalytic reaction stage of the process is carried out is generally at least 60° C. It is preferably at least 80° C. It generally does not exceed 160° C. It preferably does not exceed 140° C.

The reaction between the hydrogen fluoride and the chlorinated or chlorofluorinated precursor of the hydrofluoroalkane of the catalytic reaction stage of the process is preferably carried out in the liquid phase. In this case, the pressure is chosen so as to keep the reaction mixture in the liquid form. The pressure employed in the reaction of the catalytic reaction stage of the process varies according to the temperature of the reaction mixture. It is generally less than or equal to 35 bar. In a particularly advantageous way, the pressure is less than or equal to 25 bar. The pressure is generally greater than or equal to 5 bar. The pressure is preferably greater than or equal to 10 bar.

The catalytic reaction stage of the preparation process according to the invention can be carried out batchwise or continuously.

When the catalytic reaction stage of the preparation process according to the invention is carried out batchwise, the duration of the reaction generally varies from 10 min to 5 h. This duration is preferably at least 0.5 h. This duration is advantageously at least 1 h. This duration generally does not exceed 4 h. This duration preferably does not exceed 2.5 h.

When the catalytic reaction stage of the preparation process according to the invention is carried out continuously, the residence time of the reactants in the reactor is generally at least 0.5 h. It usually does not exceed 50 h. It typically varies from 10 to 40 h. It is preferably from 10 to 30 h.

When the preparation process according to the invention is applied to the preparation of 1,1,1,3,3-pentafluorobutane, the catalytic reaction is preferably carried out in the presence of titanium tetrachloride or of tin tetrachloride as catalyst, more particularly in the presence of titanium tetrachloride. Good results have been obtained at a temperature of 80 to 140° C., at a pressure which varies from 10 to 25 bar and with a residence time of the reactants in the catalytic reactor of 1 to 5 h.

The reaction of the catalytic reaction stage of the preparation process according to the invention can be carried out in any reactor constructed from a material which is resistant to the temperature, to the pressure and to the reactants which are used, in particular to hydrogen fluoride.

A mixture of hydrogen chloride and of hydrofluoroalkane/hydrogen fluoride is drawn off at the outlet of the catalytic reaction stage of the process, preferably in the gas phase, if appropriate with an azeotropic composition, which mixture feeds the non-catalytic reaction stage of the preparation process according to the invention, optionally after separation of the hydrogen chloride which it comprises.

An advantageous technique consists in carrying out the catalytic reaction in a boiling reactor at a temperature and a pressure such that the hydrogen chloride and the hydrofluoroalkane which are formed are gaseous, whereas the reactants and other reaction products are essentially in the liquid state. The boiling reactor is advantageously surmounted by a distillation column, in order to complete the separation. To prevent the accumulation of non-volatile impurities in the reactor and to maintain the activity of the catalyst, the reactor of the catalytic reaction stage of the process is advantageously provided with a bleed.

A specific embodiment of the preparation process according to the invention relates to a process for the preparation of a hydrofluoroalkane, according to which, in a catalytic reaction stage, at least one chlorinated or chlorofluorinated precursor of the hydrofluoroalkane is reacted with hydrogen fluoride in the presence of a catalyst and, in another non-catalytic reaction stage, a hydrofluoroalkane/hydrogen fluoride mixture originating from the catalytic reaction stage is reacted with at least one chlorinated or chlorofluorinated precursor of the hydrofluoroalkane according to the separation process according to the invention described above, at least a portion of the chlorinated or chlorofluorinated precursor employed in the catalytic stage resulting from the non-catalytic stage.

When the catalyst is a titanium compound, it proved possible to synthesize the hydrofluoroalkane in a single reaction stage.

A third subject-matter of the invention is consequently a catalytic process for the manufacture of a hydrofluoroalkane, which can be used as catalytic reaction stage in the process according to the invention, in which process the catalyst is a titanium compound. Often, in the catalytic process according to the invention, the reaction is carried out in the liquid phase and the titanium compound is a titanium halide, preferably titanium tetrachloride. The conditions described above for the catalytic reaction stage of the preparation process also apply to the catalytic process according to the invention. The catalytic process according to the invention is highly suitable for the synthesis of hydrofluoroalkanes comprising from 3 to 6 carbon atoms, such as, for example, 1,1,1,3,3-pentafluoropropane and 1,1,1,3,3-pentafluorobutane. It is particularly well suited to the synthesis of 1,1,1,3,3-pentafluorobutane, preferably in one stage from 1,1,1,3,3-pentachlorobutane.

A fourth subject-matter of the present invention is a process for the synthesis of a hydrofluoroalkane, according to which at least one chlorinated or chlorofluorinated precursor of the hydrofluoroalkane, with an F/Cl atomic ratio within the precursor of less than 1, is reacted in the liquid phase with hydrogen fluoride in a liquid medium, in which medium is continuously maintained a content by weight of greater than or equal to 50% of fluorinated or chlorofluorinated organic compounds exhibiting, on average, an F/Cl atomic ratio of at least 1, preferably of at least 1.2, with particular preference of at least 1.5. This synthetic process is preferably carried out starting from a chlorinated precursor of the hydrofluoroalkane in the absence of catalyst.

For the purposes of the present invention, the term "fluorinated or chlorofluorinated organic compounds" is understood to denote in particular the desired hydrofluoroalkane and chlorofluorinated intermediates of the hydrofluoroalkane. The intention is also to denote, optionally, certain reaction byproducts and/or certain impurities introduced by the precursor employed in the synthetic process. The content by weight of fluorinated or chlorofluorinated organic compounds in the liquid mixture is preferably at least equal to 70%. In a particularly preferred way, it is at least equal to 80%. It generally does not exceed 99% by weight. It preferably does not exceed 98.5% by weight.

The operating conditions for the reaction described in the separation process according to the invention are directly applicable to the present process for the synthesis of a hydrofluoroalkane. When the present process for the synthesis of a hydrofluoroalkane is followed by the distillation stages described in the separation process according to the invention, the operating conditions are preferably such that a reaction mixture which comprises less hydrogen fluoride than in the hydrofluoroalkane/hydrogen fluoride azeotropic mixture is drawn off in the liquid phase.

This process advantageously applies to the synthesis of 1,1,1,3,3-pentafluorobutane from 1,1,1,3,3-pentachlorobutane.

When the process is applied to the synthesis of 1,1,1,3,3-pentafluorobutane, preferably, at least 50% of the liquid reaction mixture is composed of 1,1,1,3,3-pentafluorobutane and isomers of HCFC-363 and HCFC-364.

This synthetic process is advantageous because the presence in high proportions of the desired hydrofluoroalkane and of its chlorofluorinated intermediates in the liquid reaction mixture has a solvent effect on the mixture of the hydrogen fluoride and of the chlorinated or chlorofluorinated precursor of the hydrofluoroalkane, which effect makes it possible to increase the productivity of the reaction, in particular because some chlorofluorinated intermediates which are not very reactive, which accumulate in the mixture in the absence of the hydrofluoroalkane, seem to be formed in much more limited amounts under the conditions of the synthetic process according to the invention.

The invention also relates to azeotropic or pseudoazeotropic compositions composed essentially of 1.5 mol % to 27.5 mol % of 1,1,1,3,3-pentafluorobutane and of 72.5 mol % to 98.5 mol % of hydrogen fluoride.

The thermodynamic state of a fluid is fundamentally defined by four interdependent variables: the pressure (P), the temperature (T), the composition of the liquid phase (X) and the composition of the gas phase (Y). A true azeotrope is a specific system comprising two or more components for which, at a given temperature and at a given pressure, the composition of the liquid phase X is exactly equal to the composition of the gas phase Y. A pseudoazeotrope is a system comprising 2 or more components for which, at a given temperature and at a given pressure, X is substantially equal to Y. In practice, this means that the constituents of such azeotropic and pseudoazeotropic systems cannot be easily separated by distillation.

For the purposes of the present invention, the term "pseudoazeotropic mixture" means a mixture of two constituents, the boiling point of which (at a given pressure) differs from the boiling point of the true azeotrope by a maximum of 0.5° C. Mixtures with a boiling point differing from the boiling point of the true azeotrope by a maximum of 0.2° C. are preferred. Mixtures with a boiling point differing from the boiling point of the true azeotrope by a maximum of 0.1° C. are particularly preferred.

The 1,1,1,3,3-pentafluorobutane and the hydrogen fluoride form a binary azeotrope or pseudoazeotrope when their mixture comprises approximately from 72.5 to 98.5 mol % of hydrogen fluoride. Under a pressure of 1 bar, the binary composition is composed essentially of approximately 91 to 98.5 mol % of hydrogen fluoride and 1.5 to 9 mol % of 1,1,1,3,3-pentafluorobutane and exhibits a minimum boiling point of approximately 18° C. Under a pressure of 10 bar, the binary composition is composed essentially of 78 to 85 mol % of hydrogen fluoride and 15 to 22 mol % of 1,1,1,3,3-pentafluorobutane and exhibits a minimum boiling point of approximately 90° C. Under a pressure of 12 bar, the binary composition is composed essentially of approximately 75 to 84 mol % of hydrogen fluoride and 16 to 25 mol % of 1,1,1,3,3-pentafluorobutane and exhibits a minimum boiling point of approximately 97° C.

The marked change in the concentration of the constituents of the azeotrope with the pressure is entirely unexpected. It is thus possible, by using the process according to the invention, to isolate the essentially pure constituents of the azeotrope and azeotropic fractions at a given pressure enriched either in hydrogen fluoride or in 1,1,1,3,3-pentafluorobutane.

The compositions according to the invention can be used, for example, for the purification of 1,1,1,3,3-pentafluorobutane. When it is desired to purify 1,1,1,3,3-pentafluorobutane comprising impurities which do not form an azeotrope with hydrogen fluoride or which have an azeotrope with hydrogen fluoride exhibiting a boiling point markedly different from that of the compositions according to the invention, it is possible to use the compositions to separate 1,1,1,3,3-pentafluorobutane and hydrogen fluoride, on the one hand, and the impurities, on the other hand. An example of such a use is the separation of 1,1,1,3,3-pentafluorobutane and of hydrogen fluoride from a reaction mixture obtained in a process for the synthesis of 1,1,1,3,3-pentafluorobutane by hydrofluorination of a chlorinated precursor, such as, for example, the process mentioned above. In this use, it is preferable to employ a composition according to the invention which is rich in 1,1,1,3,3-pentafluorobutane. The composition generally comprises at least 10 mol % of 1,1,1,3,3-pentafluorobutane. The composition more often comprises at least 15 mol % of 1,1,1,3,3-pentafluorobutane. it preferably comprises at least 20 mol % of 1,1,1,3,3-pentafluorobutane.

FIGS. 1 to 4 respectively illustrate specific embodiments of the process for the separation of a mixture comprising at least one hydrofluoroalkane and hydrogen fluoride, of the process for the manufacture of a hydrofluoroalkane and the azeotropic or pseudoazeotropic compositions in accordance with the present invention.

FIG. 1 illustrates the alternative form of the separation process according to the invention in which the reaction between the hydrofluoroalkane/hydrogen fluoride mixture and the organic compound, in this case a chlorinated or chlorofluorinated precursor of the hydrofluoroalkane, is carried out in the absence of catalyst.

In the plant as represented diagrammatically in FIG. 1, the chlorinated or chlorofluorinated precursor of the hydrofluoroalkane originating from a tank (1) is introduced via a route (2) into a reactor (5). The hydrofluoroalkane/hydrogen fluoride mixture to be separated according to the invention originating from a tank (3) is introduced via a route (4) into the reactor (5). In the reactor (5), the hydrogen fluoride of the hydrofluoroalkane/hydrogen fluoride mixture reacts with the chlorinated or chlorofluorinated precursor of the hydrofluoroalkane to give a mixture of reaction products comprising hydrofluoroalkane, a reduced amount of hydrogen fluoride, hydrogen chloride, chlorofluorinated intermediates, possibly unreacted chlorinated or chlorofluorinated precursor and non-volatile impurities. The hydrogen chloride is drawn off in the gaseous form from the mixture of the other reaction products via the route (6), separated, in the separator (7), from the other reaction products possibly entrained and drawn off via the route (8). The other reaction products possibly entrained return to the reactor (5) via the route (9).

The mixture of the other reaction products is conveyed in the liquid form via the route (10) to a distillation stage (11). A mixture comprising hydrofluoroalkane and hydrogen fluoride is collected at the top of the distillation (12), which mixture is optionally recycled to the reactor (5) via the route (12). A mixture of products mainly comprising hydrofluoroalkane, chlorofluorinated intermediates of the hydrofluoroalkane, possibly unreacted precursor and non-volatile impurities is collected at the bottom of the distillation (13).

Figure 2:
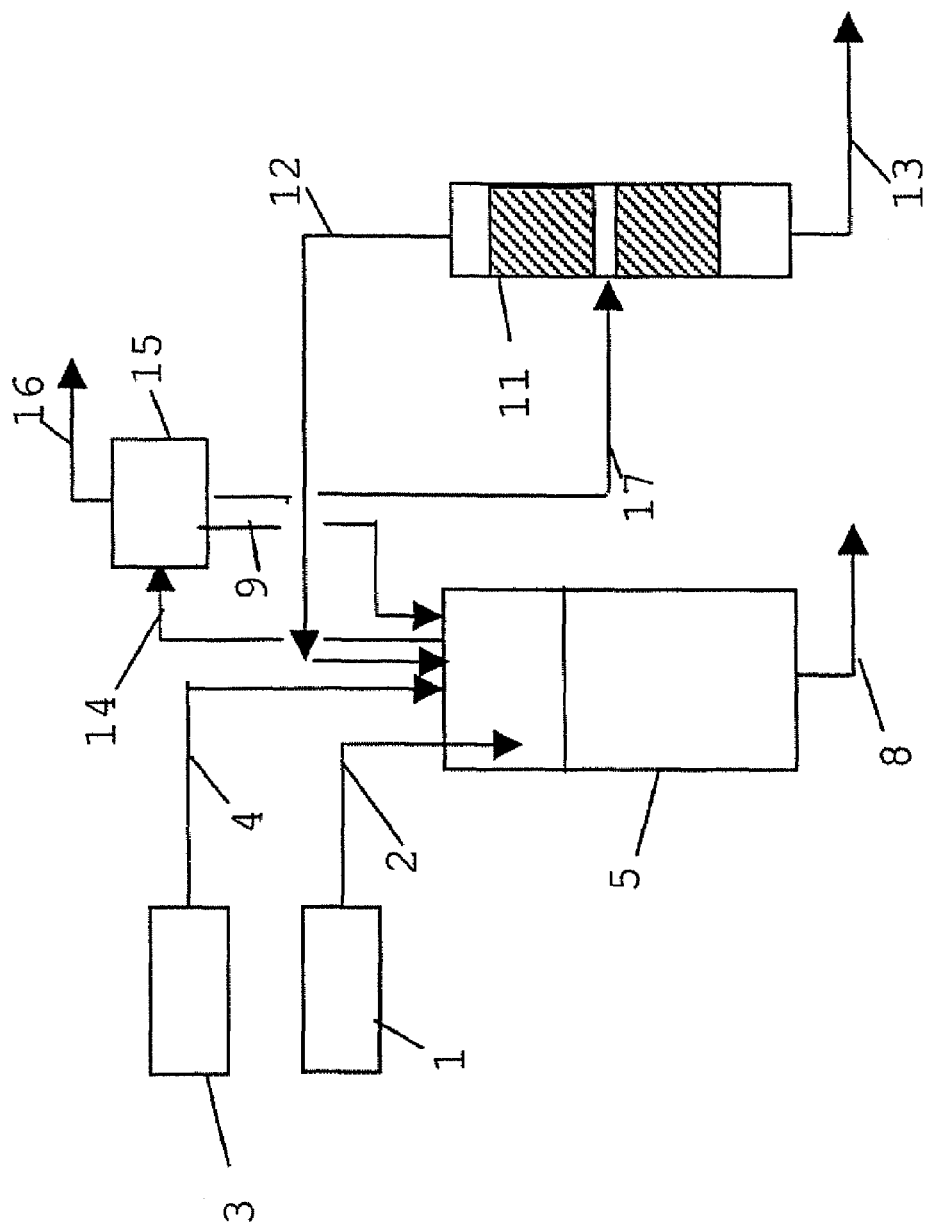

FIG. 2 illustrates the alternative form of the separation process according to the invention in which the reaction between the hydrofluoroalkane/hydrogen fluoride mixture and the organic compound, in this case a chlorinated or chlorofluorinated precursor of the hydrofluoroalkane, is carried out in the presence of a catalyst. The parts of this plant which are identical to those of the plant described in FIG. 1 carry the same reference numbers. These parts will not be described again.

In this alternative form, the reaction products of the reaction are drawn off in the gaseous form via the route (14) and are conveyed to the separator (15). The hydrogen chloride is drawn off via the route (16). The other reaction products are conveyed via the route (17) to a distillation stage (11). A mixture comprising hydrofluoroalkane and hydrogen fluoride is collected at the top of the distillation (12), which mixture is optionally recycled to the reactor (5) via the route (12). A mixture of products mainly comprising hydrofluoroalkane, chlorofluorinated intermediates of the hydrofluoroalkane, possibly unreacted precursor and non-volatile impurities is collected at the bottom of the distillation (13).

To prevent the accumulation of the non-volatile impurities in the reactor (5) and to maintain the activity of the catalyst, the reactor (5) is provided with a bleed (8).

Figure 3:
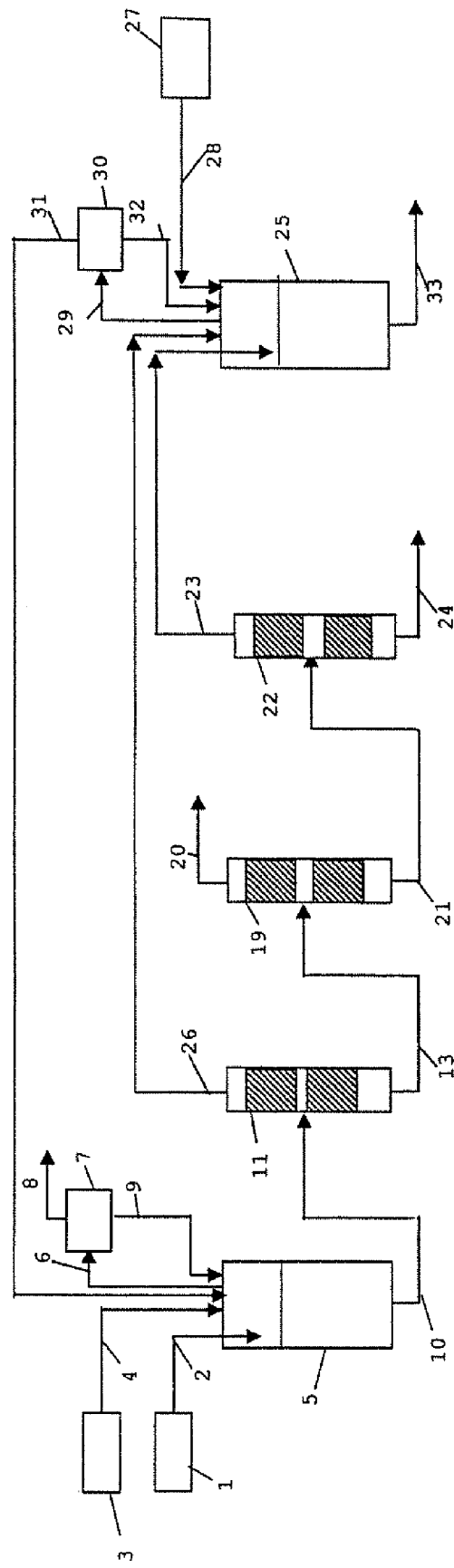

The process for the preparation of the hydrofluoroalkane in two reaction stages according to the invention is illustrated by the reaction diagram given in FIG. 3.

The parts of this plant which are identical to those of the plant described in FIG. 1 carry the same reference numbers. These parts will not be described again.

The mixture of products mainly comprising hydrofluoroalkane, chlorofluorinated intermediates of the hydrofluoroalkane, possibly unreacted precursor and non-volatile impurities collected via the route (13) is introduced into the distillation (19). The essentially pure hydrofluoroalkane is collected at the top of the distillation (20). A mixture comprising hydrofluoroalkane, chlorofluorinated intermediates of the hydrofluoroalkane, non-volatile impurities and possibly unreacted precursor is collected at the bottom of the distillation (21), which mixture is conveyed to a third distillation (22).

A mixture comprising hydrofluoroalkane, chlorofluorinated intermediates of the hydrofluoroalkane and possibly unreacted precursor is collected at the top of the distillation (23). The non-volatile impurities are collected at the bottom of the distillation (24) and are discharged from the plant.

The mixture of products collected at the top of the distillation (22) is conveyed to a catalytic reactor (25) via the route (23). In addition, unlike the plant described in FIG. 1, the mixture of hydrofluoroalkane and of hydrogen fluoride collected at the top of the column (11) is also conveyed to the reactor (25) via the route (26).

The reactor (25), which comprises a catalyst, is fed via the route (28) with hydrogen fluoride originating from the tank (27). The hydrogen fluoride reacts in the reactor (25) with the products originating from the column (22). A hydrofluoroalkane/hydrogen fluoride and hydrogen chloride mixture is drawn off from the reactor (25) in the gaseous form via the route (29) and introduced into a separator (30). The hydrofluoroalkane/hydrogen fluoride and hydrogen chloride mixture is conveyed via the route (31) to the reactor (5). The other reaction products return to the reactor (25) via the route (32).

To prevent the accumulation of the non-volatile impurities in the reactor and to maintain the activity of the catalyst, the reactor (25) is provided with a bleed (33).

The examples which follow are intended to illustrate the present invention without, however, limiting the scope thereof.

In Example 1 below, the degree of conversion (DC) of the 1,1,1,3,3-pentachlorobutane (PCBa) is the ratio, expressed as percent, of the amount employed, minus the amount unconverted on completion of the reaction, to the amount employed.

EXAMPLE 1

Example 1 was carried out in a plant in accordance with FIG. 1. 5.02 mol of hydrogen fluoride, in the form of a mixture with an azeotropic composition comprising 0.475 mol of 1,1,1,3,3-pentafluorobutane (HF/1,1,1,3,3-pentafluorobutane molar ratio of 10.6 mol/mole), and 0.739 mol of 1,1,1,3,3-pentachlorobutane were introduced into a 0.51 stainless steel reactor equipped with a mechanical paddle stirrer, a temperature probe and a dip pipe allowing samples of the liquid phase to be withdrawn during the test. The reactor was subsequently immersed in a thermostatically controlled bath, maintained at a temperature of 120° C., with continuous stirring. The pressure was regulated at 25 bar. Samples were withdrawn after reacting for 1 h, 3 h and 30 h. The results are shown in the Table below. The degree of conversion of the 1,1,1,3,3-pentachlorobutane employed varied from 94 to 100 mol %, respectively, between reacting for 1 h and 30 h. The HF/1,1,1,3,3-pentafluorobutane molar ratio fell from 6 to 1.8 mol/mole, respectively, between reacting for 1 h and 30 h. The amounts of 1,1,1,3,3-pentafluorobutane (HFC-365 mfc) and of the chlorofluorinated intermediates (HCFC-361, -362, -363 and -364) present in the reaction mixture after withdrawing the various samples are also shown.

TABLE

|  | Duration of reaction, h | | |
|---|---|---|---|
|  | 1 | 3 | 30 |
| DC PCBa, % | 94 | >99.9 | 100 |
| Amount of HFC-365mfc, mol (in the reaction mixture) | 0.51 | 0.64 | 0.99 |
| Amount of the HCFCs-364, mol (in the reaction mixture) | 0.30 | 0.35 | 0.074 |
| Amount of the HCFCs-363, mol (in the reaction mixture) | 0.09 | 0.13 | 0.10 |
| Amount of the HCFCs-362, mol (in the reaction mixture) | 0.16 | 0.04 | <0.007 |
| Amount of the HCFCs-361, mol (in the reaction mixture) | 0.007 | <0.007 | <0.007 |
| HF consumed, mol | 1.94 | 2.70 | 3.20 |
| HF remaining, mol | 3.08 | 2.30 | 1.80 |
| HF/HFC-365mfc, mol/mole | 6.0 | 3.6 | 1.8 |

EXAMPLE 2

5.0 mol of hydrogen fluoride and 0.053 mol of titanium tetrachloride were introduced into the same reactor as in Example 1. The reactor was subsequently immersed in a thermostatically controlled bath and maintained at a temperature of 135° C. with continuous stirring. The pressure was regulated at 25 bar. The reactor was continuously fed with 0.1 mol/h of 1,1,1,3,3-pentachlorobutane and 1 mol/h of hydrogen fluoride. The reactor was continuously degassed, so as to keep the level of the reaction mixture in the reactor essentially constant. The amount of 1,1,1,3,3-pentafluorobutane in the gases drawn off corresponded to a yield, with respect to the amount of 1,1,1,3,3-pentachlorobutane employed, of 97%.

The reaction was carried out over 30 hours under these conditions and the yield was stable.

The gases drawn off were a hydrogen fluoride/1,1,1,3,3-pentafluorobutane mixture in a molar ratio of approximately 5/1 which can advantageously be employed in the separation process according to the invention.

Examples 3 to 5 in FIG. 4 represent the vapour/liquid equilibria of binary compositions of 1,1,1,3,3-pentafluorobutane and of hydrogen fluoride at three different pressures. x HF means the molar proportion of hydrogen fluoride in the liquid phase and y HF means the molar proportion of hydrogen fluoride in the gas phase. The data on which the curves are based were obtained by calculation, using the Aspen Plus® software from the company Aspen Tech®, from measured and calculated thermodynamic properties of mixtures of 1,1,1,3,3-pentafluorobutane and of hydrogen fluoride. Example 3 is given by the curves corresponding to a pressure of 1 bar. Example 4 is given by the curves corresponding to a pressure of 10 bar. Example 5 is given by the curves corresponding to a pressure of 15 bar.

The invention is:

1. A process for the manufacture of 1,1,1,3,3-pentafluorobutane, which comprises reacting a chlorinated precursor with hydrogen fluoride to produce 1,1,1,3,3-pentafluorobutane and separating the 1,1,1,3,3-pentafluorobutane by using an azeotropic or pseudo-azeotropic composition which comprises 1.5 mol % to 27.5 mol % of 1,1,1,3,3-pentafluorobutane and 72.5 mol % to 98.5 mol % of hydrogen fluoride.

2. The process according to claim 1, wherein the composition is used for the purification of 1,1,1,3,3-pentafluorobutane.

3. The process according to claim 1, wherein the composition is used for separation of 1,1,1,3,3-pentafluorobutane and of hydrogen fluoride from a reaction mixture.

4. The process according to claim 1, which comprises synthezising 1,1,1,3,3-pentafluorobutane by hydrofluorination of a chlorinated precursor.

5. The process according to claim 2, which comprises synthezising 1,1,1,3,3-pentafluorobutane by hydrofluorination of a chlorinated precursor.

6. The process according to claim 3, which comprises synthezising 1,1,1,3,3-pentatluorobutane by hydrofluorination of a chlorinated precursor.

7. The process according to claim 1, wherein under a pressure of one bar the azeotropic or the pseudo-azeotropic composition comprises 1.5 mol % to 9 mol % of 1,1,1,3,3-pentafluorobutane and 91 mol % to 98.5 mol % of hydrogen fluoride.

8. The process according to claim 1, wherein the azeotropic or the pseudo-azeotropic composition comprises 1.5 mol % to 9 mol % of 1,1,1,3,3-pentafluorobutane and 91 mol % to 98.5 mol % of hydrogen fluoride.

9. The process according to claim 1, wherein the azeotropic or the pseudo-azeotropic composition comprises 15 mol % to 22 mol % of 1,1,1,3,3-pentafluorobutane and 78 mol % to 85 mol % of hydrogen fluoride.

10. The process according to claim 1, wherein the azeotropic or the pseudo-azeotropic composition comprises 16 mol % to 25 mol % of 1,1,1,3,3-pentafluorobutane and 75 mol % to 84 mol % of hydrogen fluoride.

11. In a process for the manufacture of 1,1,1,3,3-pentafluorobutane wherein the improvement comprises separating impurities from 1,1,1,3,3-pentafluorobutane by using an azeotropic or pseudo-azeotropic composition which comprises 1.5 mol % to 27.5 mol % of 1,1,1,3,3-pentafluorobutane and 72.5 mol % to 98.5 mol % of hydrogen fluoride.

12. The process according to claim 11, wherein the composition is used for the purification of 1,1,1,3,3-pentafluorobutane.

13. The process according to claim 11, wherein the composition is used for separation of 1,1,1,3,3-pentafluorobutane and of hydrogen fluoride from a reaction mixture.

14. The process according to claim 11, which comprises synthezising 1,1,1,3,3-pentafluorobutane by hydrofluorination of a chlorinated precursor.

15. The process according to claim 11, wherein under a pressure of one bar the azeotropic or the pseudo-azeotropic composition comprises 1.5 mol % to 9 mol % of 1,1,1,3,3-pentafluorobutane and 91 mol % to 98.5 mol % of hydrogen fluoride.

16. The process according to claim 11, wherein the azeotropic or the pseudo-azeotropic composition comprises 1.5 mol % to 9 mol % of 1,1,1,3,3-pentafluorobutane and 91 mol % to 98.5 mol % of hydrogen fluoride.

17. The process according to claim 11, wherein the azeotropic or the pseudo-azeotropic composition comprises 15 mol % to 22 mol % of 1,1,1,3,3-pentafluorobutane and 78 mol % to 85 mol % of hydrogen fluoride.

18. The process according to claim 11, wherein the azeotropic or the pseudo-azeotropic composition comprises 16 mol % to 25 mol % of 1,1,1,3,3-pentafluorobutane and 75 mol % to 84 mol % of hydrogen fluoride.

19. A process for the purification of 1,1,1,3,3-pentafluorobutane which comprises impurities which comprises separating the impurities which do not form an azeotrope with hydrogen fluoride or which have an azeotrope with hydrogen fluoride by using an azeotropic or pseudo-azeotropic composition which comprises 1.5 mol % to 27.5 mol % of 1,1,1,3,3-pentafluorobutane and 72.5 mol % to 98.5 mol % of hydrogen fluoride and said impurities exhibit a boiling point markedly different from said azeotropic or pseudo-azeotropic composition and to separate the 1,1,1,3,3-pentafluorobutane and hydrogen fluoride.

20. The process as claimed in claim 19, wherein the separation of 1,1,1,3,3-pentafluorobutane and of hydrogen fluoride is from a reaction mixture obtained in a process for the synthesis of 1,1,1,3,3-pentafluorobutane by hydrofluorination of a chlorinated precursor.

* * * * *